United States Patent
Dasgupta

(10) Patent No.: US 12,024,539 B1
(45) Date of Patent: Jul. 2, 2024

(54) INVENTION OF NON-HOMOLOGOUS PEPTIDE SEQUENCES TO INTERACT WITH AMYLOID BETA AND ITS PRECURSOR PROTEIN APP BY USING COMPUTER MODELING

(71) Applicant: Subhajit Dasgupta, Charleston, SC (US)

(72) Inventor: Subhajit Dasgupta, Charleston, SC (US)

( * ) Notice: Subject to any disclaimer, the term of this patent is extended or adjusted under 35 U.S.C. 154(b) by 0 days.

(21) Appl. No.: 17/090,365

(22) Filed: Nov. 5, 2020

Related U.S. Application Data

(60) Provisional application No. 62/941,021, filed on Nov. 27, 2019.

(51) Int. Cl.
*C07K 14/00* (2006.01)
*G16B 5/00* (2019.01)

(52) U.S. Cl.
CPC .............. *C07K 14/001* (2013.01); *G16B 5/00* (2019.02)

(58) Field of Classification Search
None
See application file for complete search history.

*Primary Examiner* — Sudhakar Katakam
*Assistant Examiner* — Zachary J Miknis

(57) ABSTRACT

The invented non-homologous peptide sequences are able to form dimers with corresponding amyloid beta (Aβ), its precursor protein (APP) and enzyme gamma secretase (GSA) as observed by using fixed z-axis overlay computer modeling. [The dipole moment values of these dimeric peptide structures are increased with respect to individual Aβ peptide (1-42) and APP fragments].

3 Claims, 16 Drawing Sheets

Figure 9:
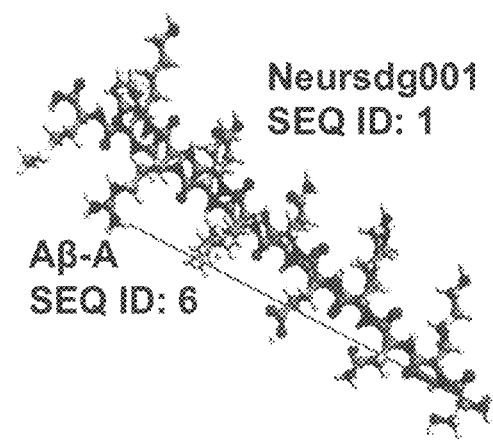

Specification includes a Sequence Listing.

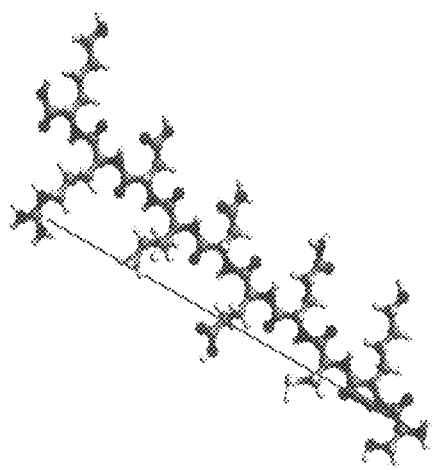
Fig.1 Neursdg001 SEQ ID: 1

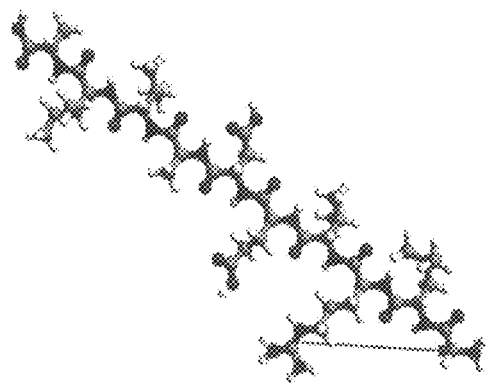
Fig.2 Neursdg002 SEQ ID: 2

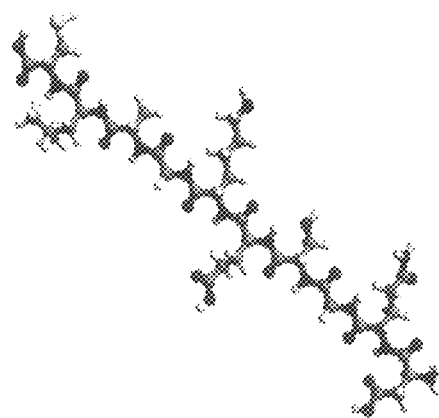
Fig.3  Neursdg003 SEQ ID: 3

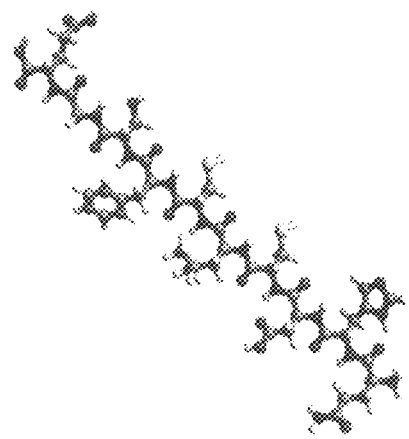
Fig.4 Neursdg004 SEQ ID: 4

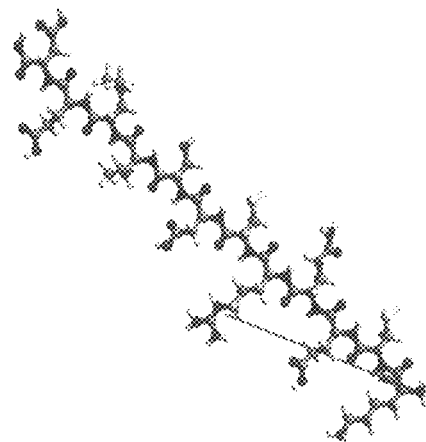
Fig.5 Neursdg005 SEQ ID: 5

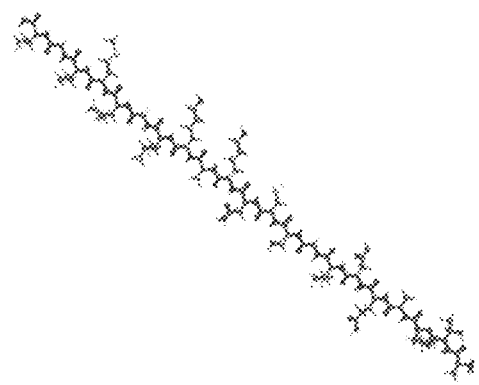
Fig.6 (Neursdg006 SEQ ID: 11)

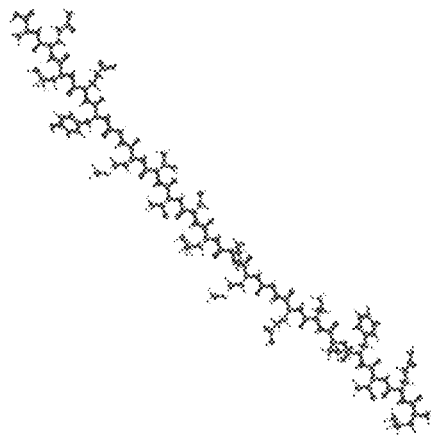
Fig.7 (Neursdg007 SEQ ID: 12)

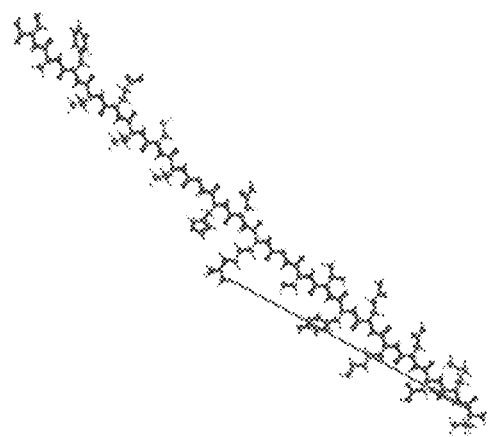
Fig.8 Neursdg008 SEQ ID: 13

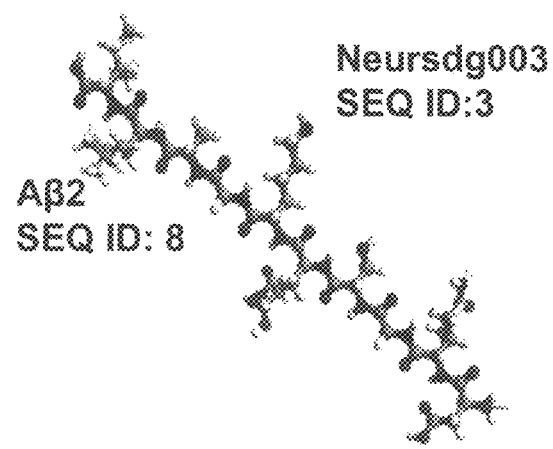
Fig.11

SEQUENCE LISTING

<160> NUMBER OF SEQ ID NOS: 22

<210> SEQ ID NO 1
<211> LENGTH: 10
<212> TYPE: PRT
<213> ORGANISM: Homo sapiens

<400> SEQUENCE: 1

Ser Lys Cys Gln Glu Asn Ile Asp Arg Lys
1               5                   10

<210> SEQ ID NO 2
<211> LENGTH: 10
<212> TYPE: PRT

<213> ORGANISM: Homo sapiens

<400> SEQUENCE: 2

Gly Leu Arg Val Glu Asp Ala Val Ile Ala
1               5                   10

<210> SEQ ID NO 3
<211> LENGTH: 10
<212> TYPE: PRT
<213> ORGANISM: Homo sapiens

<400> SEQUENCE: 3

Asp Gln Gly Ser Glu Lys Gly Ala Leu Cys
1               5                   10

<210> SEQ ID NO 4
<211> LENGTH: 10
<212> TYPE: PRT
<213> ORGANISM: Homo sapiens

<400> SEQUENCE: 4

Gln His Asp Cys Leu Cys Phe Ser Gly Glu
1               5                   10

<210> SEQ ID NO 5
<211> LENGTH: 12
<212> TYPE: PRT
<213> ORGANISM: Homo sapiens

<400> SEQUENCE: 5

Lys Cys Glu Gln Arg Cys Asp Ser Val Leu Glu Asp
1               5                   10

<210> SEQ ID NO 6
<211> LENGTH: 11
<212> TYPE: PRT
<213> ORGANISM: Homo sapiens

<400> SEQUENCE: 6

Gly Ser Asn Lys Gly Ala Ile Ile Gly Leu Met
1               5                   10

<210> SEQ ID NO 7
<211> LENGTH: 10
<212> TYPE: PRT
<213> ORGANISM: Homo sapiens

<400> SEQUENCE: 7

Gly Leu Met Val Gly Gly Val Val Ile Ala
1               5                   10

<210> SEQ ID NO 8
<211> LENGTH: 10
<212> TYPE: PRT
<213> ORGANISM: Homo sapiens

<400> SEQUENCE: 8

Asp Val Gly Ser Asn Lys Gly Ala Ile Ile
1               5                   10

<210> SEQ ID NO 9
<211> LENGTH: 10
<212> TYPE: PRT
<213> ORGANISM: Homo sapiens

```
<400> SEQUENCE: 9

His His Gln Lys Leu Val Phe Phe Ala Glu
1               5                   10

<210> SEQ ID NO 10
<211> LENGTH: 12
<212> TYPE: PRT
<213> ORGANISM: Homo sapiens

<400> SEQUENCE: 10

Asp Ala Glu Phe Arg His Asp Ser Gly Tyr Glu Val
1               5                   10

<210> SEQ ID NO 11
<211> LENGTH: 21
<212> TYPE: PRT
<213> ORGANISM: Homo sapiens

<400> SEQUENCE: 11

Ala Thr Pro Ala Glu Asp Val Gly Ser Cys Asn Lys Ala Lys Ile Gly
1               5                   10                  15

Leu Met Val Gly Val
            20

<210> SEQ ID NO 12
<211> LENGTH: 21
<212> TYPE: PRT
<213> ORGANISM: Homo sapiens

<400> SEQUENCE: 12

Leu Gln Thr Phe Pro Val Glu Gly Met Pro Leu Ser Thr Thr Met Gly
1               5                   10                  15

Tyr Glu Leu Gln Ala
            20

<210> SEQ ID NO 13
<211> LENGTH: 22
<212> TYPE: PRT
<213> ORGANISM: Homo sapiens

<400> SEQUENCE: 13

Val Leu Asp Asp Lys Gln Tyr Thr Ser Gly Arg Asn His Gly Val Cys
1               5                   10                  15

Val Glu Val Phe Ala Ser
            20

<210> SEQ ID NO 14
<211> LENGTH: 21
<212> TYPE: PRT
<213> ORGANISM: Homo sapiens

<400> SEQUENCE: 14

Phe Phe Ala Glu Asp Val Gly Ser Asn Lys Gly Ala Ile Ile Gly Leu
1               5                   10                  15

Met Val Gly Gly Val
            20

<210> SEQ ID NO 15
<211> LENGTH: 21
<212> TYPE: PRT
<213> ORGANISM: Homo sapiens

<400> SEQUENCE: 15
```

```
Ala Ala Val Thr Pro Glu Glu Arg His Leu Ser Lys Met Gln Gln Asn
1               5                   10                  15

Gly Tyr Glu Asn Pro
            20

<210> SEQ ID NO 16
<211> LENGTH: 22
<212> TYPE: PRT
<213> ORGANISM: Homo sapiens

<400> SEQUENCE: 16

Val Met Leu Lys Lys Lys Gln Tyr Thr Ser Ile His His Gly Val Val
1               5                   10                  15

Glu Val Asp Ala Ala Val
            20

<210> SEQ ID NO 17
<211> LENGTH: 25
<212> TYPE: PRT
<213> ORGANISM: Homo sapiens

<400> SEQUENCE: 17

Phe Phe Ser Phe Ile Tyr Leu Gly Glu Val Phe Lys Thr Tyr Asn Val
1               5                   10                  15

Ala Val Asp Tyr Ile Thr Val Ala Leu
            20                  25

<210> SEQ ID NO 18
<211> LENGTH: 25
<212> TYPE: PRT
<213> ORGANISM: Homo sapiens

<400> SEQUENCE: 18

Val Arg Ser Gln Asn Asp Asn Arg Glu Arg Gln Glu His Asn Asp Arg
1               5                   10                  15

Arg Ser Leu Gly His Pro Glu Pro Leu
            20                  25

<210> SEQ ID NO 19
<211> LENGTH: 26
<212> TYPE: PRT
<213> ORGANISM: Homo sapiens

<400> SEQUENCE: 19

Val Leu Leu Glu Ser Lys His Phe Thr Thr Arg Asp Leu Met Glu Lys
1               5                   10                  15

Leu Lys Gly Arg Thr Ser Arg Ile Ala Gly
            20                  25

<210> SEQ ID NO 20
<211> LENGTH: 5
<212> TYPE: PRT
<213> ORGANISM: Homo sapiens

<400> SEQUENCE: 20

Leu Val Phe Phe Ala
1               5

<210> SEQ ID NO 21
<211> LENGTH: 5
<212> TYPE: PRT
<213> ORGANISM: Homo sapiens
```

```
<400> SEQUENCE: 21

Gly Gly Val Ile Ala
1               5

<210> SEQ ID NO 22
<211> LENGTH: 5
<212> TYPE: PRT
<213> ORGANISM: Homo sapiens

<400> SEQUENCE: 22

Lys Leu Val Phe Phe
1               5
```

INVENTION OF NON-HOMOLOGOUS PEPTIDE SEQUENCES TO INTERACT WITH AMYLOID BETA AND ITS PRECURSOR PROTEIN APP BY USING COMPUTER MODELING

CROSS-REFERENCE TO RELATED APPLICATIONS

Key words/phrases: US and foreign patent search on peptide inhibitors for amyloid beta (google.com); Peptide inhibitors for amyloid beta (Google.com and PubMed.gov (NCBI) search); Peptide inhibitors and amyloid beta; peptide inhibitors and amyloid beta precursor protein; peptide inhibitor and gamma secretase; peptide inhibitor and presenilin1; peptide inhibitor and nicastrin (NCBI PubMed.gov).

Dementia is a dreadful outcome of neurodegeneration caused due to deposition of aggregated amyloid beta in various parts of brain of elderly people (24, 25, 26). Alzheimer's dementia is one of the forms which warrants medical care and treatment for cure. The FDA approved marketed Alzheimer's drugs are the modifiers of neurotransmitters and facilitate learning and memory function of brain (4, 23). But these drugs, though helpful, cannot prevent or minimize deposition and aggregation of amyloid beta (AB) in extracellular areas of brain thus, cannot block progressive neurodegeneration.

We took mission to construct peptide(s) as new therapeutic interventions to prevent or reduce generation, aggregation, and deposition of amyloid beta (1-42) responsible for Alzheimer's and related dementia. We performed extensive literature survey to find primarily any patented compound or drug either same or similar to the proposed invention we claim herewith.

We chose two search engines: www.google.com and www.pubmed.gov to find patented and peer reviewed published articles which could possibly demonstrate any peptides same or similar to the invented ones in this claim. Accordingly, we found 438000 scholarly articles using the key words mentioned above in this section. The US National Library of Medicine (NCBI) search engine www-.pubmed.gov exhibited 8595 articles in the form of abstracts and/or full text formats. Amongst all these cross references, we found a reference: Findeis M A et al. 2001 Amyloid, 8 (4): 231-241; (PMID: 11791615) [page 5, Cross Reference Number 6] and related a few references claimed a pentapeptide inhibitor protein for amyloid beta. The published inhibitor peptide sequence is: Cholyl-LVFFA-OH [SEQ ID 20]. This sequence has similarity with one of the amyloid beta peptide sequences: HHQKLVFFAE [SEQ ID 9] we constructed for our project (Aβ chain L, 10-20). Except this one, none of our constructed peptides shows any similarity with any published or patented documents. Another PubMed.gov article (PMID 30886570) showed potential role of sequence GGVVIA [SEQ ID 21] of amyloid beta peptide in aggregation and inhibitor targeted to this sequence is beneficial in treatment of Alzheimer's disease. The sequence GGVVIA [SEQ ID 21] is a partial amyloid beta sequence we are using: GLMVGGVVIA [SEQ ID 7]. However, the non-homologous peptide construct which we propose as invention, is completely different than any of the published article. We propose the sequence GLRVEDAVIA [SEQ ID 2] as invented peptide construct [I-A β1 (32-42)].

We found eighty cross references separately when took the pentapeptide sequence: KLVFF [SEQ ID 22] as key word. All these references cited in PubMed search engine are directed towards inhibition of aggregation and deposition of amyloid beta.

We claim on one of the invented peptide sequences: QHDCLCFSGE [SEQ ID 4] is constructed and evaluated as interactive, form dimer complex with amyloid beta peptide sequence fragment: HHQKLVFFAE (ANN47479.1; 2MXU_L) [Seq ID 9] in overlay computer modeling. We define the physical parameters (hydrophobicity, dipole moments, number of atoms, number of bonds) to confirm that the overlay chemical structures are indeed interactive dimer forms of two non-homologous peptides obtained by computer modeling only.

We propose here five non-homologous peptide sequences with different physical parameters (hydrophobicity, dipole moment, number of atoms, number of bonds) constructed to interact with amyloid beta protein fragments (Table1) and three non-homologous sequences are constructed to interact with fragmented APP sequences (Table3).

We selected the most relevant cross references (numbers 1-3; 5-22: presented separately. References 4, 23-26 are general references) depicting short amino acid sequence of amyloid beta peptide and use it in different forms to establish effect of inhibitors targeted those sequences to reduce amyloid beta aggregation and deposition. The screened publications from different laboratories since 1990 till November 2019 exhibit very few references on constructing peptide-drug for Alzheimer's dementia. None of the published articles show equivalence or similarity with the invented peptides proposed in the application. However, the cross references raise importance to the proposed peptide constructs as contemporary evidence.

CROSS-REFERENCE LITERATURE SEARCH

[1] H. Amijee, C. Bate, A. Williams, J. Virdee, R. Jeggo, D. Spanswick, D. I. Scopes, J. M. Treherne, S. Mazzitelli, R. Chawner, C. E. Eyers, A J. Doig, The N-methylated peptide SEN304 powerfully inhibits Abeta(1-42) toxicity by perturbing oligomer formation, Biochemistry, 51 (2012) 8338-8352.

[2] B. M. Austen, K. E. Paleologou, S. A. Ali, M. M. Qureshi, D. Allsop, O. M. EI-Agnaf, Designing peptide inhibitors for oligomerization and toxicity of Alzheimer's beta-amyloid peptide. Biochemistry, 47 (2008) 1984-1992.

[3] O. Berthoumieu, P. M. Nguyen, M. P. Castillo-Frias, S. Ferre, B. Tarus, J. Nasica-Labouze, S. Noel, O. Saurel, C. Rampon, AJ. Doig, P. Derreumaux, P. Faller, combined experimental and simulation studies suggest a revised mode of action of the anti-Alzheimer disease drug NQ-Trp, Chemistry, 21 (2015) 12657-12666.

[4] S. G. Di Santo, F. Prinelli, F. Adorni, C. Caltagirone, M. Musicco, A meta-analysis of the efficacy of donepezil, rivastigmine, galantamine, and memantine in relation to severity of Alzheimer's disease, J Alzheimers Dis, 35 (2013) 349-361.

[5] G. Eskici, M. Gur, Computational design of new Peptide inhibitors for amyloid Beta (abeta) aggregation in Alzheimer's disease: application of a novel methodology, PLOS One, 8 (2013) e66178.

[6] MA Findeis, J. J. Lee, M. Kelley, J. D. Wakefield, M. H. Zhang, J. Chin, W. Kubasek, S. M. Molineaux, Characterization of cholyl-leu-val-phe-phe-ala-OH as an inhibitor of amyloid beta-peptide polymerization, Amyloid, 8 (2001) 231-241.

[7] M. A. Findeis, S. M. Molineaux, Design and testing of inhibitors of fibril formation, Methods Enzymol, 309 (1999) 476-488.

[8] B. S. Gadad, G. B. Britton, K. S. Rao, targeting oligomers in neurodegenerative disorders: lessons from alpha-synuclein, tau, and amyloid-beta peptide, J Alzheimers Dis, 24 Suppl 2 (2011) 223-232.

[9] C. Haass, D J. Selkoe, Soluble protein oligomers in neurodegeneration: lessons from the Alzheimer's amyloid beta-peptide, Nat Rev Mol Cell Biol, 8 (2007) 101-112.

[10] N. Kokkoni, K. Stott, H. Amijee, J. M. Mason, AJ. Doig, N-Methylated peptide inhibitors of beta-amyloid aggregation and toxicity. Optimization of the inhibitor structure, Biochemistry, 45 (2006) 9906-9918.

[11] J. Lu, Q. Cao, C. Wang, J. Zheng, F. Luo, J. Xie, Y. Li, X. Ma, L He, D. Eisenberg, J. Nowick, L Jiang, D. Li, Structure-Based Peptide Inhibitor Design of Amyloid-beta Aggregation, Front Mol Neurosci, 12 (2019) 54.

[12] A. F. McKoy, J. Chen, T. Schupbach, M. H. Hecht, A novel inhibitor of amyloid beta (Abeta) peptide aggregation: from high throughput screening to efficacy in an animal model of Alzheimer disease, J Biol Chem, 287 (2012) 38992-39000.

[13] B. Neddenriep, A. Calciano, D. Conti, E. Sauve, M. Paterson, E. Bruno, D. A. Moffet, Short Peptides as Inhibitors of Amyloid Aggregation, Open Biotechnol J, 5 (2011) 39-46.

[14] M. Perez, I. Santa-Maria, E. Tortosa, R. Cuadros, M. Del Valle, F. Hernandez, F J. Moreno, J. Avila, The role of the VQIVYK peptide in tau protein phosphorylation, J Neurochem, 103 (2007) 1447-1460.

[15] N. Qin, C. B. Li, M. N. Jin, L. H. Shi, H. Q. Duan, W. Y. Niu, Synthesis and biological activity of novel tiliroside derivants, Eur J Med Chem, 46 (2011) 5189-5195.

[16] J. Sato, T. Takahashi, H. Oshima, S. Matsumura, H. Mihara, Design of peptides that form amyloid-like fibrils capturing amyloid beta1-42 peptides. Chemistry, 13 (2007) 7745-7752.

[17] R. Scherzer-Attali, R. Pellarin, M. Convertino, A. Frydman-Marom, N. Egoz-Matia, S. Peled, M. Levy-Sakin, D. E. Shalev, A. Caflisch, E. Gazit, D. Segal, Complete phenotypic recovery of an Alzheimer's disease model by a quinone-tryptophan hybrid aggregation inhibitor, PLOS One, 5 (2010) e11101.

[18] S. A. Sievers, J. Karanicolas, H. W. Chang, A. Zhao, L Jiang, O. Zirafi, J. T. Stevens, J. Munch, D. Baker, D. Eisenberg, Structure-based design of non-natural amino-acid inhibitors of amyloid fibril formation, Nature, 475 (2011) 96-100.

[19] C. Soto, E. M. Sigurdsson, L. Morelli, R. A. Kumar, E. M. Castano, B. Frangione, Beta-sheet breaker peptides inhibit fibrillogenesis in a rat brain model of amyloidosis: implications for Alzheimer's therapy, Nat Med, 4 (1998) 822-826.

[20] T. Takahashi, H. Mihara, Peptide and protein mimetics inhibiting amyloid beta-peptide aggregation. Ace Chem Res, 41 (2008) 1309-1318.

[21] M. Taylor, S. Moore, J. Mayes, E. Parkin, M. Beeg, M. Canovi, M. Gobbi, D. M. Mann, D. Allsop, Development of a proteolytically stable retro-inverso peptide inhibitor of beta-amyloid oligomerization as a potential novel treatment for Alzheimer's disease, Biochemistry, 49 (2010) 3261-3272.

[22] L. O. Tjernberg, A. Tjernberg, N. Bark, Y. Shi, B. P. Ruzsicska, Z. Bu, J. Thyberg, D J. Callaway, assembling amyloid fibrils from designed structures containing a significant amyloid beta-peptide fragment Biochem J, 366 (2002) 343-351.

[23] A. C. Tricco, H. M. Ashoor, C. Soobiah, P. Rios, A. A. Veroniki, J. S. Hamid, J. D. Ivory, P. A. Khan, F. Yazdi, M. Ghassemi, E. Blondal, J. M. Ho, C. H. Ng, B. Hemmelgarn, S. R. Majumdar, L Perrier, S. E. Straus, Comparative Effectiveness and Safety of Cognitive Enhancers for Treating Alzheimer's Disease: Systematic Review and Network Metaanalysis, J Am Geriatr Soc, 66 (2018) 170-178.

[24] R. Vandenberghe, The relationship between amyloid deposition, neurodegeneration, and cognitive decline in dementia, Curr Neurol Neurosci Rep, 14 (2014) 498.

[25] V. L. Villemagne, S. Burnham, P. Bourgeat, B. Brown, K. A. Ellis, O. Salvado, C. Szoeke, S. L Macaulay, R. Martins, P. Maruff, D. Ames, C. C. Rowe, C. L Masters, B. Australian Imaging, G. Lifestyle Research, Amyloid beta deposition, neurodegeneration, and cognitive decline in sporadic Alzheimer's disease: a prospective cohort study, Lancet Neurol, 12(2013) 357-367.

[26] V. Wilquet, B. De Strooper, Amyloid-beta precursor protein processing in neurodegeneration, Curr Opin Neurobiol, 14 (2004) 582-588

STATEMENT OF FEDERALLY SPONSORED RESEARCH AND DEVELOPMENT

[Not Applicable].

THE NAMES OF THE PARTIES TO A JOINT RESEARCH AGREEMENT

[Not Applicable].

REFERENCE TO A SEQUENCE LISTING (COMPACT DISC)

[Sequence listing text file: Sequencelisting_ST25 (size: 4734 bytes); Created Feb. 28, 2024].

STATEMENT REGARDING PRIOR DISCLOSURES BY THE INVENTOR OR A JOINT INVENTOR

Not Applicable

BACKGROUND OF INVENTION

A. Field of Invention

Dementia is a combinatorial outcome of different clinical manifestations developed due to degenerative conditions of neurons in various parts of human brain. The major causative agent is amyloid beta (AB) [24,25,26]. The amyloid beta Aβ (amino acids 1-42) is generated by specific cleavage of transmembrane (intramembrane) fragment of amyloid precursor protein by a protein degrading enzyme (protease), called gamma secretase (GSA). The Aβ (1-42) thus produced accumulate inside brain cells (neurons and astrocytes) and secrete out latter, form aggregate and deposit in different areas of brain. Chronic deposition of Aβ (1-42) is associated with abnormal function and neurodegeneration in different areas of human brain which regulate learning capability, retention of memory, language, and speech—as found in Alzheimer's and related diseases. Still today, there is no [effective] treatment to reduce Aβ aggregation and deposition.

Current Alzheimer's drugs improve learning and memory by modifying neurotransmitter acetylcholine and receptor recognition of N-methyl D-aspartate (NMDA), a small biomolecule without any alteration of Aβ aggregation and deposition. Thus, the currently available drugs improve clinical condition by delaying the severe outcome but there is no prevention of progression of Alzheimer's disease.

The current alarming context prompted to reconsider drug discovery program for dementia, define specifics of compounds, development of new or modified therapeutic interventions. The invention of non-homologous peptides interactive to fragmented amyloid beta and its precursor protein APP by computer modeling is the first stage or platform1 for the organization NeuroDrug Research LLC in the way of Alzheimer's drug discovery research.

B. Description Related to Art Including Information Disclosed Under 37CFR 1.97 and 1.98

There are multiple parameters need attention to develop preventive strategy for dementia and Alzheimer's neurodegeneration. These are, (i) to block aggregation and deposition of Aβ (1-42); (ii) to block amyloid beta precursor protein (APP) from specific cleavage; and (iii) to block catalytic site of transmembrane (intramembrane) protease enzyme gamma secretase (GSA). We strategically consider all three target points as mentioned in platform 1.

We choose first computer modeling and biophysical parameters (hydrophobicity, dipole moments) to synthesize new non-homologous peptide sequences. Here, our objective is to determine whether the invented non-homologous peptide [(inhibitor)] sequences demonstrate to form complex/dimer with fragmented sequences of either Aβ or APP and whether fragmented APP sequences can form dimer with selected GSA peptides.

We consider the change in physical parameters (hydrophobicity, dipole moments) in complex or dimerized chemical structure(s) generated by using fixed z-axis overlay computer modeling system. As, the alterations in physical parameters of two single peptides in dimerized/complex structure are indication of close interaction and bond formation between them in their new chemical structure.

BRIEF SUMMARY OF INVENTION

The objective of the platform1 is to develop new non-homologous peptide [(inhibitor)] sequences and allow these to form complex/dimer structure with either amyloid beta (AB) or its precursor protein fragments (APP) by using computer modeling. The ball and stick three-dimensional structure configurations of each peptide are constructed individually by computer model system and taken to overlay on fixed z-axis with different protein fragments of Aβ and APP to generate a complex/dimer chemical structure. The physical parameters like hydrophobicity, dipole moments, number of atoms and bonds of each individual interacting peptide are recorded and compared with those in computer generated dimer chemical structures.

The attempt is also made to determine ability of defined fragmented APP sequences to form complex/dimer structure with peptide sequences derived from components of gamma secretase enzyme: presenilin1 (PSEN1) and nicastrin (Nicas). In the platform 1 stage, we invented peptide sequences (ID: Neursdg001 to 005): [(SEQ ID: 1-5)] and (I-APPa-Neursdg006; I-APPb-Neursdg007; I(2)-APPc Neursdg008): [(SEQ ID: 11-13)] interact with fragmented Aβ peptides [(SEQ ID: 6-9)] and APP sequences [(SEQ ID: 14-16)], respectively.

BRIEF DESCRIPTION OF THE SEVERAL VIEWS OF THE DRAWING(S)

The invented peptide sequences with identifying numbers I-aβ (highlighted rows) and sequence IDs are presented in Table1-5 under detailed description of the invention. These peptide sequences are presented as covalently bonded amino acid sequences and by convention read from amino (NH2) terminal to carboxyl (COOH) terminal amino acids. The brief descriptions of invented peptides with drawings/figures are below:

FIG. 1. I-AB—A Neursdg001 Ball and Stick structure. The invented peptide Neursdg001: SKCQENIDRK [(SEQ ID: 1)] is chemically represented as $C_{48}H_{86}N_{17}O_{18}S$. The peptide is designed to bind with Aβ (Chain A) sequence: GSNKGAIIGLM [(SEQ ID 6)] (presented in Table1). The reading frame alignment is always from amino (NH$_2$) terminal to carboxyl (COOH) terminal. The amino acids in the peptide sequence are joined together by covalent "peptide bonds" (O=C—NH—) from amino terminal to carboxyl terminal. The peptide bond is the spine of protein structure and peptides. The side chains of amino acids are protruded outside the spine. The figure shows constructed peptide with N-terminal (RHS) and C-terminal (LHS) with dipole moment D=31.520; number of atoms A=170 and number of bonds B=168.

FIG. 2. I-Aβ1 (32-42) Neursdg002 Ball and Stick structure. The second invented peptide Neursdg002: GLRVEDAVIA [(SEQ ID: 2)] has chemical structure $C_{45}H_{80}N_{13}O_{15}$. The peptide is designed to bind with Aβ1 (Chain L) sequence (32-42): GLMVGGVVIA [(SEQ ID: 7)] (presented in Table 1). The reading frame is from N-terminal to C-terminal and amino acids are linked together by peptide bonds starting from N-terminal. The chemical structure of invented peptide sequence is shown number of atoms A=153; number of bonds B=151; Dipole moment D=11.31.

FIG. 3. I-Aβ2 (21-31) Neursdg003 Ball and Stick structure. The third invented peptide sequence is I-Aβ2 (21-31) Neursdg003: DQGSEKGALC [(SEQ ID: 3)]; chemical structure, $C_{39}H_{66}N_{12}O_{17}S$. The peptide is designed to bind Aβ2 (Chain L) (21-31) sequence: DVGSNKGAII [(SEQ ID: 8)] (presented in Table 1). The reading frame is from N-terminal to C-terminal and amino acids are linked together by peptide bonds starting from N-terminal. The chemical structure of invented peptide sequence is shown number of atoms A=135; number of bonds B=133; Dipole moment D=0.725.

FIG. 4. I-Aβ3 (10-20) Neursdg004 Ball and Stick structure. The fourth invented peptide sequence is I-Aβ3 Neursdg004: QHDCLCFSGE [(SEQ ID: 4)]; chemical structure, $C_{46}H_{67}N_{13}O_{17}S_2$. The peptide is constructed to bind with Aβ3 (Chain L) (10-20) sequence: HHQKLVFFAE [(SEQ ID: 9)] (Table 1). The chemical structure of the invented peptide sequence is shown with number of atoms A=145, number of bond B=145, Dipole moment D=16.88.

FIG. 5. I-Aβ4a (1-12) Neursdg005 Ball and Stick structure. The fifth invented peptide sequence is I-Aβ4a Neursdg005: KCEQRCDSVLED [(SEQ ID: 5)] with chemical structure, $C_{55}H_{94}N_{17}O_{23}S_2$. The invented peptide is constructed to bind with Aβ4a (Chain L) sequence: DAEFRHDSGYEV [(SEQ ID: 10)] (Table 1). The chemical structure of Neursdg005 shows number of atoms A=191, number of bonds B=188, Dipole moment D=17.429.

The abovementioned invented peptide sequences presented in Table1 are tested by computer modeling for fixed z-axis overlay to determine dimer structure formed with fragmented amyloid beta peptides (amyloid beta chain A and L). The Table 2 shows the test results.

The Table3 presents invented peptide sequences (I-APP a, b, and c) amyloid beta precursor peptide. The invented I-APP peptides are presented below:

FIG. 6. I-APPa Neursdg006 Ball and Stick structure. The twenty-one amino acid peptide I-APPa-Neursdg006: ATPAEDVGSCNKAKIGLMVGV [(SEQ ID: 11)]; the chemical structure can be written as, $C_{87}H_{150}N_{24}O_{29}S_2$. The peptide is constructed to bind with APPa 21 amino acid sequence: FFAEDVGSNKGAIIGLMVGGV [(SEQ ID: 14)] (Table 3). The invented peptide has number of atoms A=292, number of bonds B=291, Dipole moment D=1.315.

Likewise, the other invented I-APP peptides are:

FIG. 7. I-APPb Neursdg007 Ball and Stick structure. The twenty-one amino acid peptide I-APPb Neursdg007: LQTFPVEGMPLSTTMGYELQA [(SEQ ID: 12)] is constructed to bind with 21 amino acid sequence APPb: AAVTPEERHLSKMQQNGYENP [(SEQ ID: 15)] (Table 3). The peptide is presented with N-terminal (RHS) and C-terminal side (LHS). The chemical structure of I-APPb is, $C_{103}H_{161}N_{23}O_{33}S_2$. The invented peptide has number of atoms A=322, number of bonds B-323, Dipole moment D=0.807.

FIG. 8. I(2)-APPc-Neursdg008 Ball and Stick structure. The twenty-two amino acid I(2)-APPc peptide sequence: VLDDKQYTSGRNHGVCVEVFAS [(SEQ ID: 13)] is designed to bind with APPc amino acid sequence: VMLKKKQYTSIHHGVVEVDAAV [(SEQ ID: 16)]. The chemical structure of invented peptide I(2)APPc is $C_{104}H_{163}N_{30}O_{35}S$, number of atom A=333, number of bond B=334 and Dipole moment D=355.

The invented I-APP peptide sequences [(SEQ ID: 11-13)] are also tested individually by using computer modeling and fixed z-axis overlay to determine whether they form dimer structures with APP fragments a, b and c [(SEQ ID: 14-16)] derived from protein database.

The Tables 2, 4 and FIGS. 9-16 show the results of the overlay dimeric complex as composite chemical structures formed by invented inhibitor peptides (I-peptides) and target amyloid beta peptides.

Descriptions of the dimeric structure figures are presented below:

FIG. 9. Dimer complex formed between I-Aβ-A Neursdg001 and Aβ-A (Ball and Stick structure). The computer modeling shows invented peptide I-Aβ-A [(SEQ ID: 1)] form dimer complex with Aβ-A peptide [(SEQ ID: 6)] (Chain A). The N-terminal of the peptide dimer is located at RHS while the C-terminal is located at LIS. The number of atoms in the dimer A=324, number of bonds B=321, Dipole moment D=30.983 (Table 2).

Figure 10:
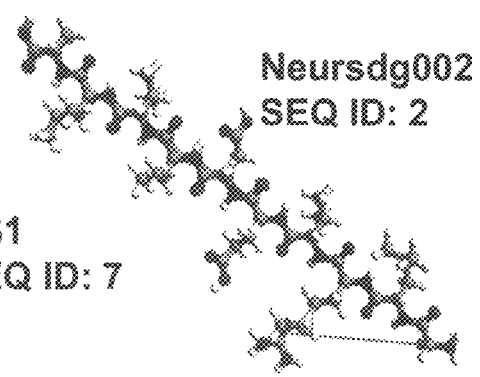

FIG. 10. Dimer complex between I-Aβ1 Neursdg002 and Aβ1 (Ball and Stick structure). The computer modeling determines dimeric structure formed between invented peptide I-Aβ1 [(SEQ ID: 2)] and Aβ1 (Chain L) [(SEQ ID: 7)]. The dimer structure shows number of atoms A=290, number of bonds B=287, Dipole moment D=11.127 (Table 2). The structure exhibits its N-terminal at RHS and C-terminal at LHS.

FIG. 11. Dimer complex between I-Aβ2 Neursdg003 and Aβ2 (Ball and Stick structure). The dimer structure formed between I-Aβ2 [(SEQ ID: 3)] and Aβ2 [(SEQ ID: 8)] sequences show number of atoms A=275, number of bonds B=272 and Dipole moment D=1.475 (Table 2). The structure exhibits its N-terminal at RHS and C terminal at LHS.

Figure 12:
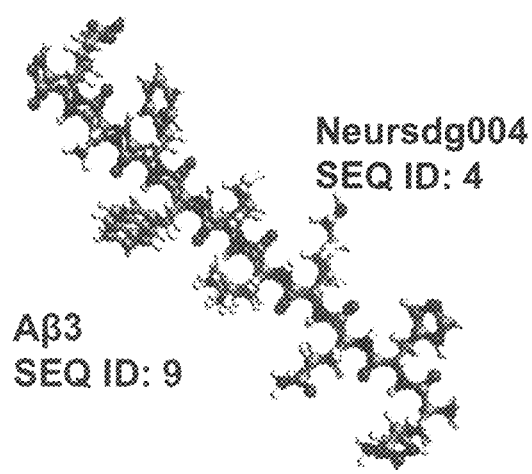

FIG. 12. Dimer complex between I-Aβ3 Neursdg004 and Aβ3 (Ball and Stick structure). The dimeric structure formed between I-Aβ3 [(SEQ ID: 4)] and Aβ3 [(SEQ ID: 9)] peptides show number of atoms A=321, number of bond B=323, Dipole moment D=1.091 (Table 2). The structure exhibits its N-terminal at RHS and C terminal at LHS.

Figure 13:
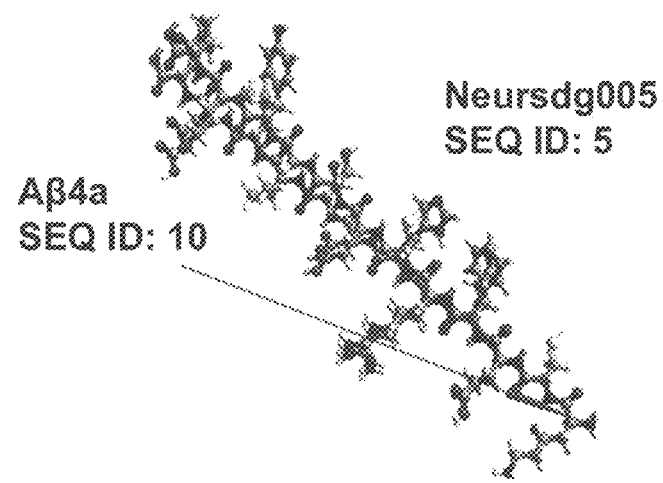

FIG. 13. Dimer structure formed between I-Aβ4a Neursdg005 and Aβ4a (Ball and Stick structure). The dimer structure formed between I-Aβ4a [(SEQ ID: 5)] and Aβ4a [(SEQ ID: 10)] shows number of atoms A=378, number of bond B=375, Dipole moment D=34.498 (Table 2). The structure exhibits its N-terminal at RHS and C terminal at LHS.

Figure 14:
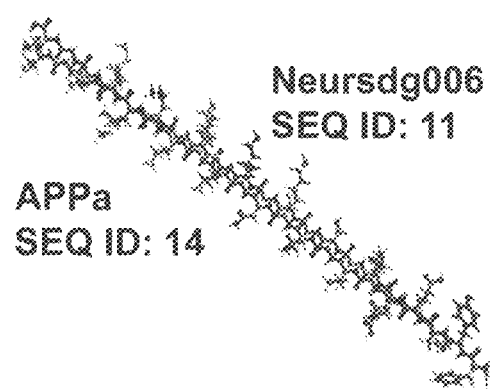

FIG. 14. Dimer structure is formed between I-APPa Neursdg006 and APPa (Ball and Stick structure). The dimeric structure formed between I-APPa [(SEQ ID: 11)] and APPa [(SEQ ID: 14)] shows number of atoms A=594, number of bond B=594 and Dipole moment D=2.716 (Table 4). The structure exhibits its N-terminal at RHS and C terminal as LHS.

Figure 15:
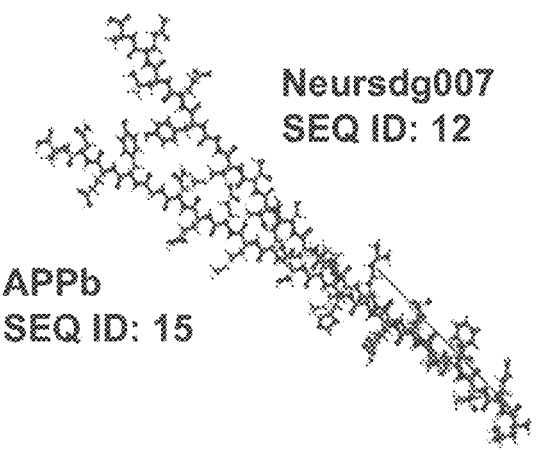

FIG. 15. Dimer structure is formed between I-APPb Neursdg007 and APPb (Ball and Stick structure). The dimeric complex between I-APPb [(SEQ ID: 12)] and APPb [(SEQ ID: 15)] structures show number of atoms A=652, number of bonds B=653 and dipole moment D=28.496 (Table 4). The structure exhibits its N-terminal at RHS and C terminal at LHS.

Figure 16:
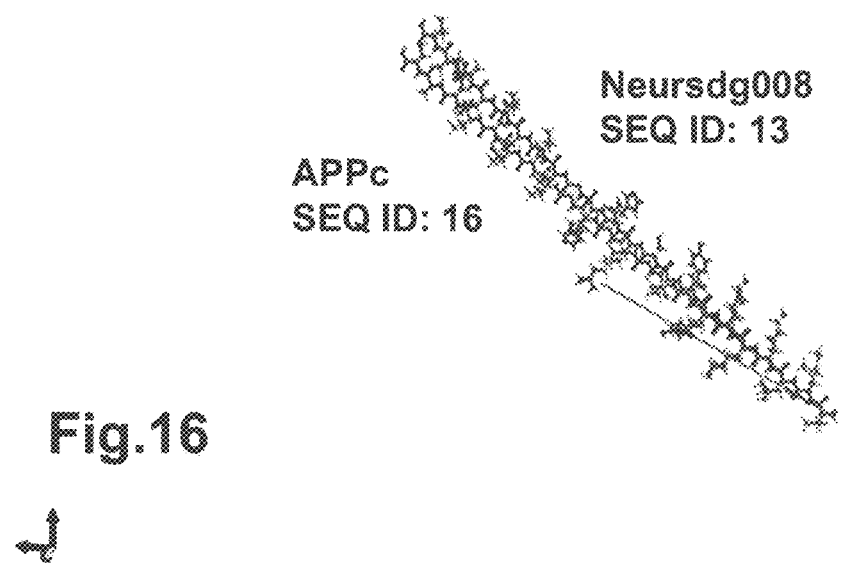

FIG. 16. Dimer structure is formed between I(2)-APPc Neursdg008 and APPc (Ball and Stick structure). The dimeric structure between I(2)-APPc [(SEQ ID: 13)] and APPc [(SEQ ID: 16)] shows number of atoms A=687, number of bonds B=689 and Dipole moment D=38.069 (Table 4). The structure exhibits its N-terminal at RHS and C terminal at LHS.

DETAILED DESCRIPTION OF INVENTION

A. Identification of Amyloid Beta (Aβ) Peptide Sequence from Protein Database

The invented five different peptides are designed by random shuffling of amino acid sequences by computer modeling technique (Table1). These peptide sequences are non-homologous to protein database derived amyloid beta sequences. The physical parameters like hydrophobicity, isoelectric point (pH) of the peptides is determined by using freely available software called, Pepdraw. The dipole moments, number of atoms and number of bonds of the same sequences are obtained by using another free software (Avogadro). The computer modeling is used to obtain three-dimensional overlay form of chemical structures of dimerized/complexed peptides. The dipole moment and hydrophobicity values with number of atoms and bonds in single peptides are obtained automatically from computer derived sequence analysis and documented in Table 1. The highlighted sequences are the invented peptides under proposition.

These invented peptides are tested for formation of dimer structure in fixed axis overlay modeling. Table2 and figures presented the constructed dimers formed by overlay of Z-axis aligned non-homologous peptide and amyloid beta peptide fragments.

9.A.1. Procedures for Constructing Invented Peptide Sequences.

Step 1. Selection of Appropriate Database in NCBI PubMed Site.

In NCBI PubMed, protein database has been selected for the purpose. The key word for feeding search engine is "HUMAN AMYLOID BETA" OR "*HOMO SAPIENS AMYLOID BETA.*" *By clicking "enter" button, the search engine will lead to a page source which contains* 2949 related and unrelated information on protein sequences.

We selected a Genebank resource title: amyloid beta A4 protein isoform a precursor [*Homo sapiens*].

The Accession number: ANN47479.1 and Gene Identity: 1040736956 are recorded.

Step II. Selection of Protein Sequence from Database.

We selected the 770 amino acid sequence (Coding Sequence: CDS 1-770) for screening out 42 amino acid amyloid beta sequence ranging from 661 amino acid position to 771.

Step III. Run Protein Blast.

The 770 amino acid sequence was fed into Blast engine for analysis and homology determination. The protein blast of this non redundant (nr) sequence (blastp) is run under specific job title.

The description section of the Blastp search engine provides one hundred related sequences.

Step IV. Selection of Protein Sequence ANA47479.1 and go for Alignment.

The Alignment search engine provides several sequence IDs with different matches in a wide range of related sequences found in mammalian system. The sequence ID ANN47479.1 is selected as desired sequence and saved separately.

In order to confirm the amyloid beta peptide sequence from the ANN47479.1 sequence, the protein data base PDB 2MXU_L is searched in addition. The search result in NCBI protein database will exhibit "Chain L, Amyloid beta A4 protein".

This is the 42 amino acid amyloid beta peptide sequence used as template to design: unique non-homologous peptide and allowed to form dimer shown by computer modeling software.

Step V. The Design of Unique Peptides (Neursdg001-005) Corresponding to Randomized Fragmented 42 Amino Acid Amyloid Beta Sequences (I-A β-A Chain A and I-A β1, 2, 3, 4a Chain L).

The 42 amino acid amyloid beta (Aβ) peptide was fragmented into 10 amino acid containing sequences obtained from different protein data base sources (NCBI). The I-Aβ-A (Neursdg001) is obtained from PDB: 1QCM_A (chain A). The rest sequences are from chain L (2MXU_L) (Table 1).

The amino sequence of each I-A-β peptide (highlighted in Table 1) has been shuffled randomly and put in a software PepDraw (free software). The software provides length, mass, isoelectric point (pH at which net charge is neutral), net charge, hydrophobicity, and extinction coefficient.

9.A.2. Experiment by Using Overlay Computer Modeling to Determine Interaction Between Non-Homologous Invented Peptides and Fragmented Amyloid Beta Peptides.

9.A.2.i. Test to Determine Overlay Pattern of Invented Non-Homologous Peptide and Amyloid Beta Peptide Fragment at Fixed Aligned Z-Axis to Form Dimer in Computer Model.

The constructed novel I-Aβ peptides and 10 amino acid Aβ peptide sequences are analyzed in Avogadro peptide analysis and drawing software (free software) individually. The ball and stick three-dimensional structure models are used to construct the single and overlay dimerized peptide structures. The number of atoms and bonds in the structure are calculated automatically by the software system. The estimated dipole moment (measure of net polarity of positive and negative charge in an inorganic or organic compound) for each peptide and overlaid dimer structure are calculated and presented by the software (Table 2). The figures of each dimer are presented after Table 2 for invented peptides interact with amyloid beta.

Outline of Avogadro software operation. The Avogadro software has provision to calculate bond length and number of atoms in the structure. The automatic calculations are found under "view" section within "property" sub section of the software. The "build" section and "peptide" sub section within it are used to construct peptide structure for analysis.

TABLE 1

The non-homologous newly constructed I-Aβ peptide sequences are presented in relation to NCBI database-derived fragmented amyloid beta (Aβ)

| Name and sequence ID of Aβ-sequences | Sequence ID | Peptide Sequences ($NH_2$-terminal: LHS; COOH-terminal: RHS) | Chemical formula | Hydrophobicity* KCAL/MOL | Dipole moment (D)# | Atoms (A) and Bonds (B) |
|---|---|---|---|---|---|---|
| I-Aβ-A [(SEQ ID: 1)] | Neursdg001 | SKCQENIDRK | $C_{48}H_{36}N_{17}O_{18}S$ | 23.52 | 31.520 | A: 170<br>B: 168 |
| Aβ A (Chain A) [(SEQ ID: 6)] | PDB: IQCM_A GI: 159162888 | GSNKGAIIGLM | $C_{45}H_{81}N_{13}O_{14}S$ | 11.80 | 10.373 | A: 154<br>B: 153 |
| I-A β1 (32-42) [(SEQ ID: 2)] | Neursdg002 | GLRVEDAVIA | $C_{45}H_{80}N_{13}O_{15}$ | 15.84 | 11.31 | A: 153<br>B: 151 |
| A β1 (Chain L) (32-42) [(SEQ ID: | PDB: ANN47479.1/ 2MXU_L GI: | GLMVGGVVIA | $C_{41}H_{74}N_{10}O_{11}S$ | 7.43 | 9.899 | A: 137<br>B: 136 |

TABLE 1-continued

The non-homologous newly constructed I-Aβ peptide sequences are presented in relation to NCBI database-derived fragmented amyloid beta (Aβ)

| Name and sequence ID of Aβ-sequences | Sequence ID | Peptide Sequences (NH$_2$-terminal: LHS; COOH-terminal: RHS) | Chemical formula | Hydrophobicity* KCAL/MOL | Dipole moment (D)# | Atoms (A) and Bonds (B) |
|---|---|---|---|---|---|---|
| 7)]<br>I-A β2<br>(21-31)<br>[(SEQ ID: 3)] | 817598550<br>Neursdg003 | DQGSEKGALC | $C_{39}H_{66}N_{12}O_{17}S$ | 20.73 | 0.725 | A: 135<br>B: 133 |
| A β2<br>(Chain L)<br>(21-31)<br>[(SEQ ID: 8)] | PDB:<br>ANN47479.1/<br>2MXU_L<br>GI:<br>817598550 | DVGSNKGAII | $C_{41}H_{72}N_{12}O_{15}$ | 15.75 | 6.865 | A: 140<br>B: 139 |
| I A β3<br>(10-20)<br>[(SEQ ID: 4)] | Neursdg004 | QHDCLCFSGE | $C_{46}H_{67}N_{13}O_{17}S_2$ | 16.88 | 0.923 | A: 145<br>B: 145 |
| A β 3<br>(Chain L)<br>(10-20)<br>[(Seq ID: 9)] | PDB:<br>ANN47479.1/<br>2MXU_L<br>GI:<br>817598550 | HHQKLVFFAE | $C_{60}H_{86}N_{16}O_{14}$ | 15.13 | 0.304 | A: 176<br>B: 178 |
| I-A β4a<br>(1-12)<br>[(SEQ ID: 5)] | Neursdg005 | KCEQRCDSVLED | $C_{55}H_{94}N_{17}O_{23}S_2$ | 26.53 | 17.429 | A: 191<br>B: 188 |
| A β 4a<br>(Chain L)<br>(1-12)<br>[(SEQ ID: 10)] | PDB:<br>ANN47479.1/<br>2MXU_L<br>GI:<br>817598550 | DAEFRHDSGYEV | $C_{61}H_{86}N_{17}O_{23}$ | 25.81 | 16.951 | A: 187<br>B: 187 |

TABLE 2

The Chemical structures of peptide dimers constructed by overlay of I-Aβ and Aβ non-homologous peptides

| Sequences | Aβ A (Chain A) | A β1 (Chain L) (amino acid: 32-42) | A β2 (Chain L) (amino acid: 21-31) | A β 3 (Chain L) (amino acid: 10-20) | A β 4a (Chain L) (amino acid: 1-12) |
|---|---|---|---|---|---|
| I-A β -A | $C_{93}H_{167}N_{30}O_{32}S_2$<br>D:30.983;<br>A:324;<br>B:321 | | | | |
| I-A β1 (32-42) | | $C_{86}H_{154}N_{23}O_{26}S$<br>D:11.127;<br>A:290; B:287 | | | |
| I- A β2 (21-31) | | | $C_{80}H_{138}N_{24}O_{32}S$<br>D:1.475;<br>A:275;<br>B:272 | | |
| IA β3 (10-20) | | | | $C_{106}H_{153}N_{29}O_{31}S_2$<br>D:1.091; A:321;<br>B:323 | |
| I-A β4a (1-12) | | | | | $C_{116}H_{180}N_{34}O_{46}S_2$<br>D:34.498;<br>A:378;B:375 |

Dipole moment (D) defines separation of charges or partial charges in an inorganic or organic compound.

9.A.2.ii. Test to Determine Overlay Pattern of Invented Peptide and Amyloid Beta Precursor Protein (APP) Fragment at Fixed Aligned Z-Axis to Form Dimer in Computer Model In a similar procedure, the non-homologues peptide sequences are constructed for amyloid precursor protein (APP). The key word phrases "Amyloid precursor protein and *Homo sapiens*" are used to search contents in protein database (NCBI PubMed). The sequence ID AAB26265.2 Length 82; NP_000475.1 Length 770 are selected to screen efficacy of invented peptide sequences to form dimer. All these and invented non-homologous peptides (highlighted) are presented in Table3.

The computer modeling overlay of the non-homologous peptides with corresponding APP sequence template to form dimer construct structural formula is shown in the Table 4.

TABLE 3

The non-homologous newly constructed I-APP sequences (highlighted) are presented in relation to fragmented APP sequences derived from NCBI database 770 amino acid APP isoform a precursor (*Homo sapiens*)

| Sequence | Sequence ID | Peptide Sequences (NH2 terminal: LHS; COOH-terminal: RHS) | Chemical formula | Hydrophobicity* KCAL/MOL | Dipole moment# | Atoms (A) and Bonds (B) |
|---|---|---|---|---|---|---|
| I-APPa [(SEQ ID: 11)] | I-APPa-Neursdg006 | ATPAEDVGSCNKAKIGLMVGV (21 AMINO ACIDS) | $C_{87}H_{150}N_{24}O_{29}S_2$ | 22.98 | 1.315 | A: 292; B: 291 |
| APPa [(SEQ ID: 14)] | AAB26265.2 | FFAEDVGSNKGAIIGLMVGGV (21 AMINO ACIDS)) | $C_{94}H_{149}N_{23}O_{28}S$ | 17.07 | 1.111 | A: 295; B: 295 |
| I-APPb [(SEQ ID: 12)] | I-APPb-Neursdg007 | LQTFPVEGMPLSTTMGYELQA (21 AMINO ACIDS) | $C_{103}H_{161}N_{23}O_{33}S_2$ | 13.02 | 0.807 | A: 322; B: 323 |
| APPb [(SEQ ID: 15)] | NP_000475.1 | AAVTPEERHLSKMQQNGYENP (21 AMINO ACIDS) | $C_{101}H_{160}N_{31}O_{35}S$ | 29.02 | 28.015 | A: 328; B: 328 |
| I(2)-APPc [(SEQ ID: 13)] | I(2)-APPc-Neursdg008 | VLDDKQYTSGRNHGVCVEVFAS (22 AMINO ACIDS) | $C_{104}H_{163}N_{30}O_{35}S$ | 25.81 | 38.378 | A: 333; B: 334 |
| APPc I(SEQ ID: 16)] | NP_000475.1 | VMLKKKQYTSIHHGVVEVDAAV (22 AMINO ACIDS) | $C_{110}H_{182}N_{30}O_{31}S$ | 25.81 | 0.956 | A: 354; B: 355 |

Dipole moment defines separation of charges or partial charges in an inorganic or organic compound.

The amino acid sequence IDs are provided in the left column—Sequence (Table 3).

TABLE 4

The chemical structures of peptide dimers constructed by overlay of non-homologous peptide I-APP (a, b, and c) with identified APP protein fragments (APP a, b, and c)

| Sequences | APPa AAB26265.2 | APPb NP_000475.1 | APPc NP_000475.1 |
|---|---|---|---|
| I-APPa Neursdg006 | $C_{186}H_{301}N_{47}O_{57}S_3$ D: 2.716; A: 594; B: 594 | | |
| I-APPb Neursdg007 | | $C_{204}H_{322}N_{55}O_{68}S_3$ D: 28.496; A: 652; B: 653 | |
| I(2)-APPc Neursdg008 | | | $C_{214}H_{345}N_{60}O_{66}S_2$ D:38.069; A:687; B:689 |

FIGS. 14, 15 and 16 demonstrate interaction between invented peptides (I-APP) and protein data base derived APP fragments evaluated by using fixed z-axis overlay computer modeling.

9.A.2.iii. Test to Determine Overlay Pattern of Amyloid Beta Precursor Protein (APP) Fragment and Peptide Sequences Selected from Presinilin1 (PSEN1) and Nicastrin Components of Enzyme Gamma Secretase at Fixed Aligned Z-Axis to Form Dimer in Computer Model In addition, we analyze the physical parameters and use computer modeling to evaluate if the protein database derived fragmented APP sequences (APP a, b, and c) form any dimer/complex with components of protease enzyme gamma secretase (GSA): presinilin1 (PSEN1) and nicastrin (Nicas). The concept is, the substrate APP must bind with catalytic side of GSA to form an enzyme-substrate complex which lower the reaction energy level and catalyze the reaction to drive forward to form product. The experiment will determine the closest interaction and/or dimer formation between NCBI database derived APP sequences (a, b, c) and PSEN1 (b, c) or Nicas (a1) sequences.

Table5 presents the identified APP, PSEN1 and nicastrin sequences and their overlaid composite dimer structures constructed by computer modeling taking a fixed Z-axis.

TABLE 5

Computer modeling on fixed z-axis chemical structures of dimers constructed through overlay between identified fragmented APP sequences and gamma secretase components presenilin (PSEN1); Nicastrin sequence a1

| Gamma secretase (GSA) components selected for test | APP sequence-a FFAEDVGSNKGAIIGLMVGGV [SEQ ID 14] | APP sequence-b AAVTPEERHLSKMQQNGYENP [SEQ ID 15] | APP sequence-c VMLKKKQYTSIHHGVVEV DAAV [SEQ ID 16] |
|---|---|---|---|
| PSEN1 (sequence-b) ID: AAB05895.1 FFSFIYLGEVFKTYNVAVDYITVAL [(Seq ID: 17)] Chemical structure $C_{145}H_{207}N_{27}O_{37}$ A:416; B:421; D:1.604; H:6.38 KCAL/MOL | $C_{239}H_{356}N_{50}O_{65}S$ D:2.660 A:711; B: 716 | $C_{248}H_{367}N_{59}O_{72}S$ D:26.438 A:744; B:749 | $C_{255}H_{389}N_{57}O_{68}S$ D:1.599 A:770; B:776 |
| PSEN1 (sequence-c) ID: AAF19253.1 VRSQNDNRERQEHNDRRSLGHPEPL [(Seq ID: 18)] Chemical structure $C_{122}H_{204}N_{49}O_{43}$ A:418; B:418; D:185.436; H:43.26 KCAL/MOL | $C_{216}H_{353}N_{72}O_{71}S$ D:184.706 A:713; B:713 | $C_{223}H_{264}N_{80}O_{78}S$ D:212.913 A:746; B: 746 | $C_{232}H_{386}N_{79}O_{74}S$ D:185.159 A:772; B:773 |
| Nicastrin (sequence_a1) ID:NP_056146.1 VLLESKHFTTRDLMEKLKGRTSRIAG [(Seq ID: 19)] Chemical structure $C_{130}H_{227}N_{40}O_{38}S$ A:422; B:421; D:181.088; H: 30.22 KCAL/MOL | $C_{240}H_{409}N_{70}O_{69}S_2$ D:191.734 A:790; B:790 | $C_{231}H_{387}N_{71}O_{73}S_2$ D:219.290 A:764; B:763 | $C_{240}H_{409}N_{70}O_{69}S_2$ D:191.869; B:790; B:790 |

The chemical structures of dimers found following overlay of two non-homologous peptide sequences in a fixed z-axis are mentioned in the Table5 check boxes.

This has been found; the identified APP sequences interact with selected PSEN1 and nicastrin sequences and exhibit formation of a dimer with alteration in their individual dipole moment, number of atoms and number of bonds. The sequence IDs for each amino acid sequences are mentioned in the parenthesis in the left-Gamma Secretase component-column (Table 5).

9.B. Analysis of Observations

The computer modeling is used to identify interaction of non-homologues invented peptides with parent amyloid beta or its precursor protein sequences. The two freely available educational software systems Pepdraw and Avogadro are used [initially] to determine peptide length, mass, hydrophobicity, isoelectric point, dipole moment, number of atoms and bonds formed in single as well as computer modeling derived dimer peptide constructs. As we see, the hydrophobicity and dipole moment are inversely related for a peptide or protein molecule.

The invention claimed is:

1. The heterodimeric structures are formed between each non-homologous peptide sequence and its corresponding Amyloid beta fragment as follows: [SEQ ID 1] and [SEQ ID 6], [SEQ ID 2] and [SEQ ID 7], [SEQ ID 3] and [SEQ ID 8], [SEQ ID 4] and [SEQ ID 9], and [SEQ ID 5] and [SEQ ID 10].

2. Non-homologous peptide sequences [SEQ ID numbers: 11, 12, 13] construct heterodimeric structures with their corresponding amyloid beta precursor protein (APP) fragments, resulting in the following pairs: [SEQ ID 11] and [SEQ ID 14], [SEQ ID 12] and [SEQ ID 15], [SEQ ID 13] and [SEQ ID 16].

3. All of the amyloid beta precursor proteins (APP) [SEQ ID 14], [SEQ ID 15], and [SEQ ID 16] can bind and form heterodimers with the peptide sequences of Presenilin-1 sequence-b [SEQ 17], Presenilin-1 sequence-c [SEQ 18], and Nicastrin sequence-a1: [SEQ 19].

* * * * *